United States Patent [19]

Schibler et al.

[11] 3,953,505

[45] Apr. 27, 1976

[54] CARBAMIDE-FORMALDEHYDE CONDENSATION PRODUCTS, THEIR MANUFACTURE AND USE

[75] Inventors: Luzius Schibler, Riehen; Jurg Merz, Therwil, both of Switzerland

[73] Assignee: Ciba-Geigy Corporation, Ardsley, N.Y.

[22] Filed: Mar. 26, 1973

[21] Appl. No.: 344,670

[30] Foreign Application Priority Data

Mar. 28, 1972  Switzerland.......................... 4632/72
Dec. 22, 1972  Switzerland....................... 18728/72

[52] U.S. Cl. ...................... 260/553 R; 260/553 E; 260/251 R; 260/248 R; 260/553 A; 252/541; 252/DIG. 1; 427/342
[51] Int. Cl.²...................................... C07C 127/15
[58] Field of Search .............................. 260/553 R

[56] References Cited
FOREIGN PATENTS OR APPLICATIONS 2,012,995   3/1970   France 38-9862   6/1963   Japan

*Primary Examiner*—James O. Thomas, Jr.
*Assistant Examiner*—G. T. Breitenstein
*Attorney, Agent, or Firm*—Joseph G. Kolodny; Prabodh I. Almaula; Edward McC. Roberts

[57] ABSTRACT

New carbamide-formaldehyde condensation products which possess at least one hydrophilic and at least one hydrophobic radical, characterised in that at least one hydrophobic radical is bonded via a

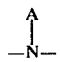

bridge, wherein A denotes hydrogen or alkyl with 1 to 4 carbon atoms, and at least one hydrophilic radical is bonded via a N-methylol-ether bridge, to a cyclic or acyclic urea radical, these products are particularly useful as reactive surface-active agents.

6 Claims, No Drawings

CARBAMIDE-FORMALDEHYDE CONDENSATION PRODUCTS, THEIR MANUFACTURE AND USE

The invention relates to carbamide-formaldehyde condensation products which possess at least one hydrophilic and at least one hydrophobic radical, characterised in that at least one hydrophobic radical is bonded via a

bridge, wherein A denotes hydrogen or alkyl with 1 to 4 carbon atoms, and at least one hydrophilic radical is bonded via a N-methylolether bridge, to a cyclic or acyclic urea radical.

By a N-methylolether bridge there is to be understood, in the present case, a grouping of the formula

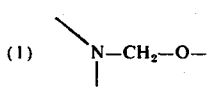

wherein the nitrogen belongs to an amino group of the urea radical and the oxygen is bonded to the hydrophilic radical. If desired, it is also possible for two methylol radicals to be bonded to one nitrogen atom.

The urea radicals of the present condensation products are above all derived from urea itself. In addition, however, cyclic ureas with 5 or 6 ring members can also be used.

Cyclic ureas correspond, for example, to the formula

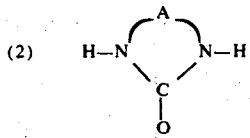

wherein A denotes an alkylene radical with 2 or 3 carbon atoms in the chain which is optionally substituted by hydroxyl, lower alkyl, lower alkoxy, lower hydroxyalkoxy or lower alkoxyalkoxy; a lower N-alkylamino- or N-hydroxyalkylamino-N,N-dimethylene radical or a 4,5-ethyleneurea radical.

Lower alkyl, hydroxyalkyl, alkoxy and hydroxyalkoxy as a rule contain at most 4 carbon atoms, for example methyl, ethyl, iso-propyl, n-butyl, hydroxyethyl, methoxy, ethoxy, n-propoxy, tert. butoxy, hydroxyethoxy or hydroxypropoxy. Lower alkoxyalkoxy preferably contains at most 4 carbon atoms in each of the two alkoxy radicals.

The cyclic ureas are preferably compounds of the formula

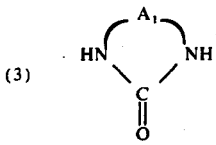

wherein $A_1$ represents a radical of the formula (3.1) —CH$_2$CH$_2$—
(3.2) —CH$_2$CH$_2$CH$_2$—
(3.3) —CHOH—CHOH—
(3.4) —CHOD—CGL—CH$_2$—
(3.5) —CH$_2$—NT—CH$_2$—   or
(3.6) 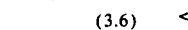
(3.7) 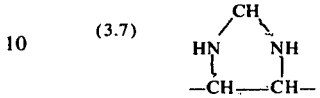

wherein D denotes hydrogen, alkyl with 1 to 4 carbon atoms, hydroxyalkyl with 2 to 4 carbon atoms or alkoxyalkyl with 1 to 4 carbon atoms in the alkoxy part and 2 to 4 carbon atoms in the alkyl part, G and L denote hydrogen or alkyl with 1 to 4 carbon atoms and T denotes alkyl with 1 to 4 carbon atoms or hydroxyalkyl with 2 to 4 carbon atoms.

Simple cyclic ureas are, for example, ethyleneurea, propyleneurea or acetylenediurea, glyoxalurea, 4-methoxy-5,5-dimethylhexahydropyrimidone-2 or N-ethyltriazone. These are preferred in the form of their methylol compounds.

The N-alkyltriazones, which also belong to the cyclic ureas, correspond, for example, to the formula

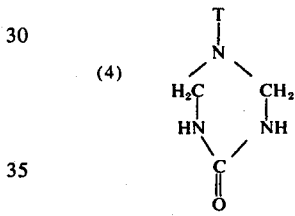

wherein T has the indicated meaning. Preferably, T represents ethyl in the formulae (3.5) and (4).

The hexahydropyrimidones which also belong here correspond preferably to the formula

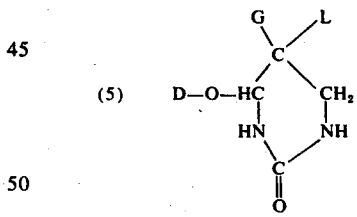

wherein D, G and L have the indicated meaning. Preferably, however, D, G and L in the formulae (3,4) and (5) are each a methyl radical.

Amongst the cyclic ureas, ethyleneurea is particularly preferred.

The hydrophobic radical in the carbamide-formaldehyde condensation product is, for example, a saturated or unsaturated, cyclic or acyclic, aliphatic radical, an aromatic radical or an araliphatic radical.

The hydrophilic radical is derived from monoalkylene glycols or polyalkylene glycols or from alkanolamines.

Advantageous condensation products contain, as the hydrophobic radical, an alkyl or alkenyl radical with 6 to 22 carbon atoms, a cycloalkyl radical with 5 or 6 ring carbon atoms, an alkylphenyl radical with 1 to 12 carbon atoms in the alkyl part, a phenyl or a benzyl radical or an acyl radical corresponding to these radicals, particularly an alkanoyl, alkenoyl or benzoyl radical, and contain, as the hydrophilic radical, a monoalkylene glycol or polyalkylene glycol radical with an average molecular weight of at most 2,000, especially 62 or 105 to 2,000, or above all 105 to 1,500.

Compounds of particular interest are carbamide-formaldehyde condensation products of the formula

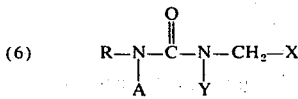

(6)  R—N—C—N—CH$_2$—X
       |       |
       A       Y wherein R is alkyl, alkenyl, alkylcarbonyl or alkenylcarbonyl with 6 to 22 carbon atoms, cycloalkyl with 5 or 6 ring carbon atoms, alkylphenyl with 1 to 12 carbon atoms in the alkyl radical, phenyl, benzyl or benzoyl; A is hydrogen or alkyl with 1 to 4 carbon atoms; Y is hydrogen, —CH$_2$—O—Q—, wherein Q is hydrogen or alkyl with 1 to 4 carbon atoms, or —CH$_2$-X'; and X and X' each denote a monoalkylene glycol or polyalkylene glycol radical, bonded via an oxygen atom, and having an average molecular weight of at most 2,000 and 2 to 4 carbon atoms per alkylene unit.

The hydrophobic radicals or R are, for example, alkyl radicals such as n-hexyl, n-decyl, n-dodecyl, n-hexadecyl, n-octadecyl or behenyl; alkenyl radicals such as $\Delta^{9,10}$-decenyl, $\Delta^{9,10}$-dodecenyl, $\Delta^{9,10}$-hexadecenyl or $\Delta^{9,10}$-$\Delta^{12,13}$-octadecadienyl; cycloalkyl radicals such as cyclopentyl or cyclohexyl; alkylphenyl radicals such as 3,5-di-tert.butylphenyl, p-n-nonylphenyl or p-n-dodecylphenyl; phenyl or benzyl.

The alkyl radicals in the radical A are, for example, methyl, ethyl, isopropyl, n-propyl or n-butyl.

The group —CH$_2$—O-Q in the definition of Y is a methylol group which is optionally etherified with an alkanol with 1 to 4 carbon atoms. The alkanol can here be, for example, methanol, ethanol, isopropanol, n-propanol or n-butanol. Y preferably represents hydrogen, methoxymethyl or CH$_2$—X'.

The radical X is derived from monoalkylene glycols or polyalkylene glycols which as a rule possess 2 to 4, preferably 2, carbon atoms per alkylene unit. Polyalkylene glycols, including also dialkylene glycols, are preferred over monoalkylene glycols. The radical X is always bonded to the methylene group via one of its oxygen atoms. The alkylene glycol radicals can furthermore be terminally etherified with an alkanol with at most 4 carbon atoms, for example with n-butanol, n-propanol, ethanol or especially methanol. The non-etherified products are, however, preferred. The radicals X are derived, for example, from ethylene glycol, diethylene glycol, polyethylene glycol, 1,3-propylene glycol, 1,2-propylene glycol, polypropylene glycol or polybutylene glycol.

A preferred position is occupied by condensation products of the formula

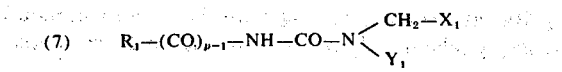

(7)  R$_1$—(CO)$_{p-1}$—NH—CO—N$\begin{matrix}CH_2-X_1\\Y_1\end{matrix}$ wherein p is 1 or 2, R$_1$ denotes alkyl or alkenyl with 6 to 22 carbon atoms, Y$_1$ denotes hydrogen, —CH$_2$OQ or —CH$_2$-X$_1$ and X$_1$ denotes a polyethylene glycol radical having an average molecular weight of 105 to 1,500 and bonded via an oxygen atom, and Q has the above-mentioned meaning. p is preferably 1 and Q in particular represents methyl.

Particularly suitable condensation products correspond to the formula

(8)  R$_2$ — NH — CO — N(CH$_2$ — X$_1$)$_2$ wherein X$_1$ has the indicated meaning and R$_2$ denotes alkyl with 10 to 18 carbon atoms.

Condensation products of the formula

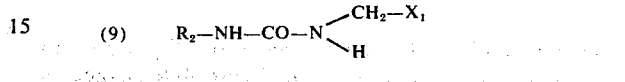

(9)  R$_2$—NH—CO—N$\begin{matrix}CH_2-X_1\\H\end{matrix}$ wherein R$_2$ and X$_1$ have the indicated meaning, are also of interest.

The carbamide-formaldehyde condensation products according to the invention are manufactured by a) reacting a cyclic or acyclic urea-formaldehyde condensation product which contains at least one hydrophobic radical bonded in the indicated manner, and which possesses at least one free N-methylol group, b) with an alkylene glycol in the presence of a weak acid, at a temperature of 80° to 120°C and at a pressure of 1 to 30 mm Hg, or c) with an alkylene oxide in the presence of a metal alcoholate of a transition metal of groups IV, V or VI of the periodic system and optionally in the presence of an alkali metal hydroxide or alkali metal alcoholate, at a temperature of 10° to 160°C and a pressure of 1 to 20 atmospheres gauge.

Acyclic urea-formaldehyde condensation products are preferred as the component a).

Components a) of particular interest are urea-formaldehyde condensation products which possess, as the hydrophobic radical according to the definition, an alkyl or alkenyl radical with 6 to 22 carbon atoms, a cycloalkyl radical with 5 or 6 ring carbon atoms, an alkylphenyl radical with 1 to 12 carbon atoms in the alkyl radical, a phenyl radical or a benzyl radical, or an acyl radical corresponding to these radicals.

The carbamide-formaldehyde condensation products of the formula (6) are obtained on using a compound of the formula

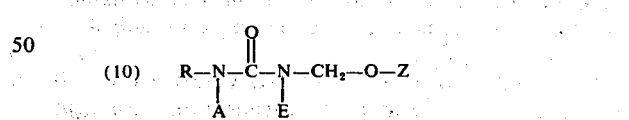

(10)  R—N—C—N—CH$_2$—O—Z
        |       |
        A       E as the component a), wherein R and A have the indicated meaning, E denotes hydrogen or —CH$_2$—O—Z' and Z and Z' each denote hydrogen or alkyl with 1 to 4 carbon atoms and at least one N-methylol group is free.

Condensation products of the formula (7) are manufactured from compounds of the formula

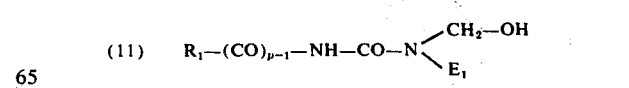

(11)  R$_1$—(CO)$_{p-1}$—NH—CO—N$\begin{matrix}CH_2-OH\\E_1\end{matrix}$ wherein E$_1$ denotes hydrogen or —CH$_2$OQ and R$_1$, Q and p have the indicated meaning.

To manufacture the condensation products of the formula (8) and (9), the component a) which is used is a compound of the formula

(12) $R_2-NH-CO-N\begin{matrix}CH_2OH\\CH_2OH\end{matrix}$ or of the formula

(13) $R_2 - NH - CO - NH - CH_2OH$ wherein $R_2$ has the indicated meaning.

The component a) is now reacted either with b) a polyalkylene glycol or c) an alkylene oxide.

Polyalkylene glycols with an average molecular weight of at most 2,000, for example of 105 to 2,000, and 2 to 4 carbon atoms per alkylene unit, especially polyethylene glycols with an average molecular weight of 105 to 1,500 or above all of about 300, have proved advantageous as the component b).

Possible polyalkylene glycols are, for example, polybutylene glycol or especially polypropylene glycol and above all polyethylene glycol.

The reaction with b) is preferably carried out in the presence of an alkanecarboxylic acid with 1 to 3 carbon atoms as the weak acid. In addition to formic acid and propionic acid, acetic acid has above all proved advantageous here. The reaction is preferably carried out at 90° to 100°C. The pressure is preferably 10 to 25 mm Hg.

After completion of the reaction, it is advisable to neutralise the reaction product with a base. For this purpose, alkanolamines such as monoalkanolamine, dialkanolamine or especially triethanolamine can above all be used.

In the process variant wherein a reaction with the component c) is carried out, alkylene oxides are to be understood as compounds which possess an epoxide grouping. These include, for example, styrene oxide and diglycidyl ether, but preferably propylene oxide or above all ethylene oxide.

The reaction with the alkylene oxide is carried out in the presence of a metal alcoholate as the catalyst, which preferably corresponds to the formula

(17) $Me(O-Ak)_r(B)_{q-r}$ wherein Me denotes a q-valent transition metal of groups IV, V or VI of the periodic system, Ak denotes phenyl, benzyl, cycloalkyl with at most 12, especially 5 to 12, and above all 8 to 12, ring carbon atoms or preferably an optionally halogensubstituted alkyl with 1 to 4 carbon atoms, B denotes halogen, for example bromine or preferably chlorine, or alkoxy with 1 to 4 carbon atoms, r denotes 1 to q and q denotes 4, 5 or 6.

These metal alcoholates are especially alcoholates of transition metals of groups IV, V or VI of the 4th, 5th or 6th period of the periodic system according to Lange's Handbook of Chemistry, 10th edition, 1967, pages 60 and 61. These transition metals, also called elements of the intermediate groups, of the groups a or of the groups b, include titanium, zirconium, hafnium, vanadium, niobium, tantalum, chromium, molybdenum and tungsten. The radical 13 O—Ak is preferably a radical of an alkanol such as, for example, methanol, ethanol, β-chloroethanol, isopropanol, n-propanol, n-butanol, sec.- or tert.-butanol, of of phenol, benzyl alcohol or a cycloalkanol with, appropriately, 5 to 12 carbon atoms, such as cyclododecanol. As alkoxy, B as a rule differs from Ak and can denote, for example, methoxy, ethoxy, propoxy or preferably tert. butoxy. The reaction with the component c) is preferably carried out in the presence of metal alcoholates of the formula

(18) $Me_1(O-Ak_1)_q$ wherein $Me_1$ denotes niobium$^V$, tantalum$^V$, tungsten$^{VI}$, molybdenum$^{VI}$ zirconium$^{IV}$ or hafnium$^{IV}$, $Ak_1$ denotes alkyl with 1 to 4 carbon atoms and n denotes 4,5 or 6, corresponding to the valency of the metal.

Particularly suitable metal alcoholates correspond to the formula

(19) $Me_2(O-Ak'1)_q$ wherein $Me_2$ denotes zirconium$^{IV}$, niobium$^V$, tantalum$^V$ or tungsten$^{VI}$ and $q_1$ denotes 4, 5 or 6 and $Ak_1$ has the indicated meaning.

The reaction with the component c) is in particular carried out in the presence of an additional catalyst, namely in the presence of an alkali metal hydroxide or alkali metal alcoholate with an alkanol with 1 to 4 carbon atoms. Possible representatives of such catalysts are, for example, lithium hydroxide, sodium hydroxide, potassium hydroxide, rubidium hydroxide or caesium hydroxide or the corresponding alcoholates of alkanols such as indicated for the alcoholates of the transition metals.

Preferably, sodium hydroxide or potassium hydroxide or a sodium alcoholate or potassium alcoholate of an alkanol with 1 to 4 carbon atoms is used as the additional catalyst.

The metal alcoholates alone or together with the alkali metal hydroxides or alkali metal alcoholates are advantageously employed in amounts of 0.05 to 5 percent, preferably 0.1 to 2 percent or especially 0.4 to 1 percent, relative to the weight of the reaction mixture.

If the two types of catalyst are used together, the weight ratio of transition metal alcoholate to alkali metal hydroxide or alkali metal alcoholate is as a rule 9 : 1 to 1 : 9, preferably 4 : 1 to 1 : 4 or above all 7 : 3 to 3 : 7.

Typical representatives of the transition metal alcoholates are, for example:

| | |
|---|---|
| (20.1) | $Ta(OCH_3)_5$ |
| (20.2) | $Ta(OC_2H_5)_5$ |
| (20.3) | $Ta(O-CH(CH_3)_2)_5$ |
| (20.4) | $Ta(OC(CH_3)_3)_5$ |
| (20.5) | $Ta(O-$ 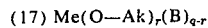 $)_5$ |
| (20.6) | $Nb(OCH_3)_5$ |
| (20.7) | $Nb(OC_2H_5)_5$ |
| (20.8) | $Nb(O-CH(CH_3)_2)_5$ |
| (20.9) | $Nb(OC(CH_3)_3)_5$ |
| (20.10) | $Nb(O-$ 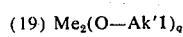 $)_5$ |
| (20.11) | $W(OCH_3)_6$ |
| (20.12) | $W(OC(CH_3)_3)_6$ |
| (20.13) | $Hf(O-CH(CH_3)_2)_4$ |
| (20.14) | $Hf(O-C(CH_3)_3)_4$ |
| (20.15) | $Mo(O-CH(CH_3)_2)_6$ |
| (20.16) | $Mo(O-C(CH_3)_3)_6$ |
| (20.17) | $Ti(OC_2H_5)_4$ |
| (20.18) | $Ti(O-C(CH_3)_3)_4$ |
| (20.19) | $Zr(OC_2H_5)_4$ |
| (20.20) | $Zr(O-C(CH_3)_3)_4$ |
| (20.21) | $Ta(OCH_3)Cl_4$ |
| (20.22) | $Nb(OCH_3)_4Cl$ |
| (20.23) | $Ti(OC_4H_9)_4$ |
| (20.24) | $Zr(OCH_2CH_2Cl)_4$ |
| (20.25) | $Ta(OCH_3)(OC(CH_3)_3)_4$ |

```
                   -continued
        (20.26)    Zr(OCH₃)Cl₃
```

Typical representatives of the alkali metal hydroxides and alkali metal alcoholates are, for example:

```
        (21.1)     LiOH
        (21.2)     NaOH
        (213)      KOH
        (21.4)     LiOCH₃
        (21.5)     NaOCH₃
        (21.6)     NaOC₂H₅
        (21.7)     NaOC(CH₃)₃
        (21.8)     KOCH₃
        (21.9)     KOC₂H₅
        (21.10)    KOC(CH₃)₃.
```

The temperature of the reaction with the component c) is preferably 30° to 120°C or especially 40° to 90°C. The reaction can be carried out at atmospheric pressure or under excess pressure. Preferably, the pressure is 1 to 15 atmospheres gauge or especially 1 to 11 atmospheres gauge. As a rule, the reaction is carried out under the so-called autogenic pressure, that is to say the pressure generated by the reaction mixture itself at the given temperature.

Depending on the end use of the reaction products, 1 to 100, preferably 1 to 25, mols of the component c) are as a rule added onto the component a).

It can at times be desirable to carry out the alkoxylation in the presence of a second alkoxide which does not participate in the actual reaction. For example, it is possible to carry out the reaction with ethylene oxide and to use propylene oxide or dioxane as the reaction medium or as the suspending medium.

The reaction with the component c) has the advantage that alkylene oxides can be directly added onto a N-methylolated urea compound under mild conditions, that is to say at low temperatures and with a practically neutral catalyst system. As is known, N-methylol compounds are unstable even in a weakly acid medium and in a strongly alkaline medium they form polycondensates or split off formaldehyde and water.

Addition reactions of, for example, ethylene oxide to an organic compound which possesses a mobile hydrogen atom are usually carried out at temperatures of 160° to 200°C. However, at such high temperatures most N-methylol compounds are no longer stable, that is to say a degradation of the methylol groups occurs. Due to the catalyst system used according to the invention (metal alcoholates alone or together with alkali metal hydroxides or alkali metal alcoholates) it has now become possible successfully to carry out such addition reactions even at relatively low temperatures, that is to say temperatures below 160°C, without a degradation of the methylol groups taking place.

The products according to the invention are in the main low molecular, nonmeric products which at most can contain minor proportions of more highly condensed products.

The carbamide-formaldehyde condensation products according to the invention are reactive surface-active agents and can be employed wherever the use of reactive surfaceactive agents appears desirable. From the aqueous solution, these reactive condensation products separate out as insoluble hydrophobic resins after acidification, that is to say at pH 1 or below about 5.

Because of their methylol groups, the products according to the invention are reactive and can be used for various purposes, depending on the substituents. In particular, they are suitable for use as reactive surface-active products which under certain conditions, for example in an acid medium or at a higher temperature, can be converted into an irreversibly insoluble state. They can thus be used, for example, in the manufacture of micro-capsules. They are furthermore distinguished by good foaming power and washing power and are suitable for use as washing agents, washing agent additives, emulsifiers, dispersing agents, additives to agents which confer a hydrophobic character, agents which confer a soft handle and a hydrophilic character, and as carriers.

The examples which follow explain the invention without restricting it thereto. In these examples, percentages are percentages by weight throughout.

EXAMPLE 1 a. 295 g of octadecyl-isocyanate are introduced in a known manner into 500 ml of toluene and thereafter ammonia gas is introduced slowly until an indicator paper clearly shows an alkaline reaction (pH = 10), whilst at the same time the desired intermediate product precipitates (after about 2 hours).

62.5 g (0.2 mol) of this octadecylurea are fused in a round-bottomed flask at 110°C and thereafter 6 g of triethanolamine are added whilst stirring (pH 8–10). 3 portions, each of 10 g (0.3 mol), of paraformaldehyde are introduced into this mixture and after 4 hours 98 g of a reaction product, smelling of formaldehyde, are obtained, which predominantly corresponds to the following formulae:

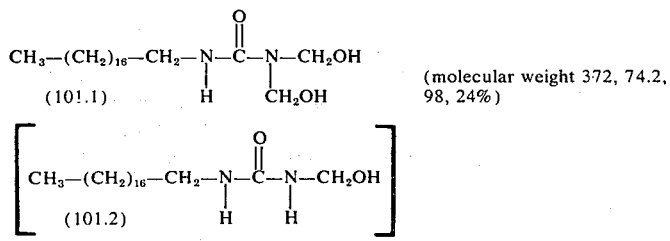

(molecular weight 372, 74.2, 98, 24%)

b. 7.1 g (0.04 mol) of this intermediate product are fused with 13.2 g (0.6 mol) of ethylene oxide and 100 mg of Ta(OC₂H₅)₅ and shaken for 16 hours in an oil bath thermostatically controlled to 80°C, whereupon 17 g of a waxy product are obtained. This corresponds to a yield of 86 percent relative to a theoretical yield of 18.6 g (after deducting the free formaldehyde). This preparation can be used both as a washing agent and as an agent for conferring hydrophobic properties.

The product in the main corresponds to the formulae

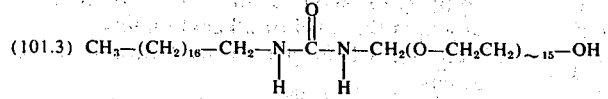

(101.3) $CH_3-(CH_2)_{16}-CH_2-NH-CO-NH-CH_2(O-CH_2CH_2)_{\sim 15}-OH$ and

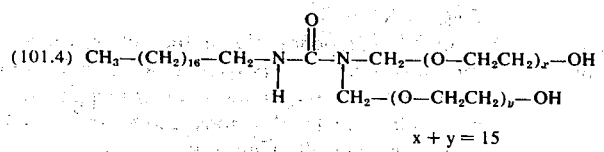

(101.4) $CH_3-(CH_2)_{16}-CH_2-N(H)-CO-N(CH_2-(O-CH_2CH_2)_x-OH)-CH_2-(O-CH_2CH_2)_y-OH$ $x + y = 15$ and

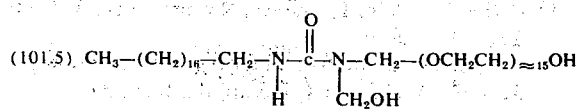

(101.5) $CH_3-(CH_2)_{16}-CH_2-N(H)-CO-N(CH_2OH)-CH_2-(OCH_2CH_2)_{\approx 15}OH$

EXAMPLE 2

Octadecylurea is manufactured in a known manner from octadecyl-isocyanate in accordance with Example 1, by addition of ammonia.

(102.1) $C_{18}H_{37}-N=C=O + NH_3 \rightarrow C_{18}H_{37}-NH-CO-NH_2$

Heating this product with paraformaldehyde in the presence of triethanolamine yields octadecylmethylolurea.

(102.2) $C_{18}H_{37}-NH-CO-NH-CH_2OH$ 1 mol of this product is condensed for 2 hours with 1 mol of polyethylene glycol of average molecular weight 1,000 in the presence of 0.15 mol of glacial acetic acid in vacuo at 90° – 100°C, in the course of which a little dilute acetic acid and formaldehyde distil off. The remainder of the glacial acetic acid is neutralised with triethanolamine and a liquid surface-active agent is obtained, which on cooling solidifies to an ointment and which easily dissolves in water to give a foaming solution. If the latter is acidified, a hydrophobic resin separates out, rapidly on heating and more slowly at room temperature. This surface-active agent corresponds in the main to the formula

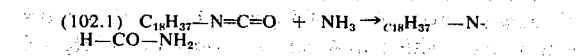

(102.3) $H_{37}C_{18}-HN-CO-NH-CH_2-G_2$ wherein $G_2$ represents a polyethylene glycol radical of average molecular weight 1,000, bonded via an oxygen atom.

EXAMPLE 3 a. 65.2 g (0.2 mol) of stearoylurea are mixed with 45 g (1.5 mols) of paraformaldehyde and 10 g of triethanolamine (pH 8–9). The paraformaldehyde is added in portions, the reaction being complete after 4½ hours. The yield is 87 g, of a compound of the formula

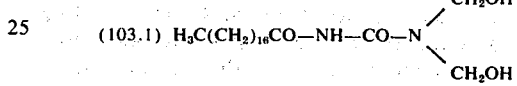

(103.1) $H_3C(CH_2)_{16}CO-NH-CO-N(CH_2OH)_2$

The determination of formaldehyde gives the following results:

| | |
|---|---|
| total $CH_2O$ | = 17% |
| free $CH_2O$ | = 4% |
| bonded $CH_2O$ | = 13%, theoretical bonded $CH_2O$ 15.5%. |

The yield of dimethylolstearoylurea is accordingly 84%.

b. 7.7 g (0.02 mol) of this intermediate product of the formula (103.1), 8.8 g (0.2 mol) of ethylene oxide and 100 mg of $Ta(OGH_2H_5)$ are sealed and shaken for 16 hours in an oil bath thermostatically controlled to 80°C, whereby 15 g of a waxy product are obtained. This corresponds to a yield of 91 percent relative to a theoretical yield of 16.5 g. This preparation gives a very good degree of whiteness when washing wool and the clarification of the washing liquor after 24 hours is very good.

The product in the main corresponds to the formula

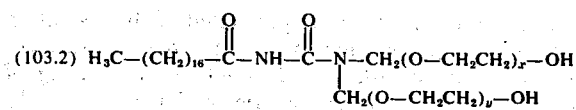

(103.2) $H_3C-(CH_2)_{16}-CO-NH-CO-N(CH_2(O-CH_2CH_2)_x-OH)-CH_2(O-CH_2CH_2)_y-OH$ $x + y = 10$

EXAMPLE 4 a. 55 g of a compound of the formula

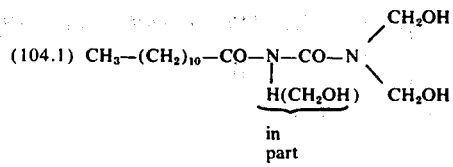

(104.1) $CH_3-(CH_2)_{10}-CO-N(H)-CO-N(H(CH_2OH))(CH_2OH) / CH_2OH$ in part which is manufactured by reaction of laurylurea with paraformaldehyde, are dissolved in 200 g of boiling methanol and adjusted to pH 3 with 4 g of 37 percent strength hydrochloric acid. The etherification is carried out for 15 minutes at 65°C. Thereafter 25 percent strength NaOH solution is added dropwise until the solution has a pH of 6.5 – 7.0. The reaction mixture is filtered off hot and and is carefully freed of excess methanol by evaporation and dried overnight in vacuo at 50°C. The yield of monoether is 53 g (95 percent of theory). The waxy preparation predominantly contains a compound of the following structural formula:

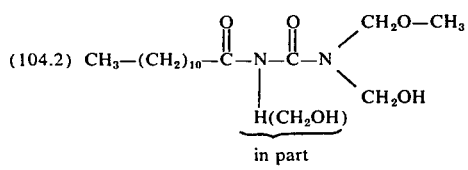

in part b. 6.4 g (0.02 mol) of this intermediate product, 8.8 g (0.2 mol) of ethylene oxide and 100 mg of Ta-$(OC_2H_5)_5$ are sealed and shaken for 20 hours in an oil bath thermostatically controlled to 80°C, whereby 13 g of a waxy product are obtained. This corresponds to a yield of 85.5 percent relative to a theoretical yield of 15.2 g. An aqueous solution of 2 g/l is clearopalescent and has a foam volume of 245 ccs and a wetting power of 8.3 seconds. The degree of whiteness of wool washed with this preparation is very good and the clarification of the wash liquor is again complete after 24 hours.

The product in the main corresponds to the formula

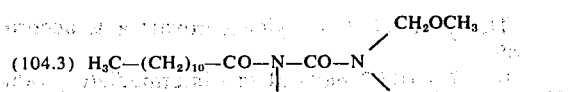

and in part to the formula

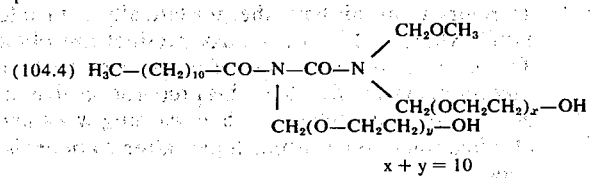

$x + y = 10$

EXAMPLE 5

If a cotton fabric is impregnated with a solution which contains, per liter, 50 g of the reactive surface-active agent according to Example 1 and 1.25 g of monoammonium phosphate, dried and heated to 150°C for 5 minutes, a hydrophobic effect is achieved which becomes even more pronounced after treatment with soap solution at 60°C. The water-repellent action also proves to be stable to trichloroethylene and when tested with n-hexane the fabric does not show a solvent ring.

We claim:

1. An urea-formaldehyde condensation product having the formula

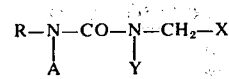

wherein
R represents alkyl, alkenyl, with 6 to 22 carbon atoms in the alkyl or alkenyl moiety,
A represents hydrogen or alkyl with 1 to 4 carbon atoms,
Y represents hydrogen, — $CH_2O$ — Q, wherein Q is hydrogen or alkyl with 1 to 4 carbon atoms, or — $CH_2$ — X′, and
X and X′, independently of the other, represent a monoalkylene or polyalkylene glycol radical, bonded via an oxygen atom, and having an average molecular weight of at most 2,000 and 2 to 4 carbon atoms per alkylene unit.

2. An urea-formaldehyde condensation product as defined in claim 1, wherein R represents alkyl with 6 to 22 carbon atoms.

3. A carbamide-formaldehyde condensation-product as defined in claim 1, having the formula

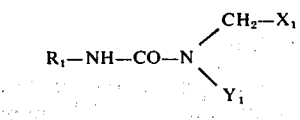

$R_1$ denotes alkyl or alkenyl with 6 to 22 carbon atoms, $Y_1$ denotes hydrogen, —$CH_2OQ$, wherein Q is hydrogen or alkyl with 1 to 4 carbon atoms, or —$CH_2$—$X_1$, and $X_1$ denotes a polyethylene glycol radical with an average molecular weight of 105 to 1,500, bonded via an oxygen atom.

4. A carbamide-formaldehyde condensation product as defined in claim 3, having the formula

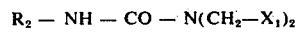

wherein $X_1$ has the meaning indicated in claim 3 and $R_2$ denotes alkyl with 10 to 18 carbon atoms.

5. A carbamide-formaldehyde condensation product as defined in claim 4, having the formulae

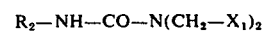

and

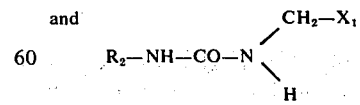

wherein $X_1$ has the meaning indicated in claim 3 and $R_2$ denotes alkyl with 10 to 18 carbon atoms.

6. A carbamide-formaldehyde condensation product as defined in claim 3, having the formulae 13
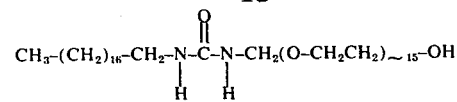
and
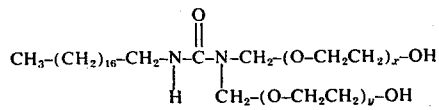
14
-continued
and
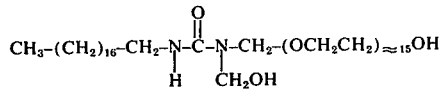
wherein $x + y$ equals 15.
* * * * *